United States Patent [19]

Raaijmakers

[11] 4,322,313

[45] Mar. 30, 1982

[54] STABILIZED MULTI-PURPOSE BLOOD DILUENT

[75] Inventor: Christiaan E. Raaijmakers, Deventer, Netherlands

[73] Assignee: J. T. Baker Chemicals B.V., Deventer, Netherlands

[21] Appl. No.: 193,095

[22] Filed: Oct. 2, 1980

[51] Int. Cl.$^3$ .................. G01N 33/16; C09K 3/00
[52] U.S. Cl. .................. 252/408; 23/230 B; 424/153; 424/343; 424/101
[58] Field of Search ............ 252/408; 23/230 B; 424/153, 343

[56] References Cited

U.S. PATENT DOCUMENTS

| | | | |
|---|---|---|---|
| 3,962,125 | 6/1976 | Armstrong | 252/408 |
| 4,102,810 | 7/1978 | Armstrong | 252/408 |
| 4,244,837 | 1/1981 | Crews et al. | 252/408 |
| 4,248,634 | 2/1981 | Forester | 252/408 |
| 4,286,963 | 9/1981 | Ledis et al. | 252/408 |

Primary Examiner—Teddy S. Gron
Attorney, Agent, or Firm—George W. Rauchfuss, Jr.

[57] ABSTRACT

A multi-purpose blood diluent for blood cells for use in electronic counting and sizing of blood cells comprising a stable water solution of chemical salts providing an electrolytic solution to which a blood sample can be added to dilute the large number of red blood cells, white blood cells and other components and enable the desired parameters of these blood components to be measured, counted and determined. The diluent is azide-free and contains a bacteriostatic agent that substantially reduces the bubble formation capable of interfering with the determinations that resulted from the prior art use of 2-phenoxyethanol as the bacteriostatic agent. The diluent employs phenylethanol as the bacteriostatic agent and lithium chloride as the agent to stabilize red blood cell volume.

3 Claims, No Drawings

STABILIZED MULTI-PURPOSE BLOOD DILUENT

FIELD OF THE INVENTION

This invention relates to a multi-purpose blood diluent for blood cells for use in electronic counting and sizing of blood cells comprising a stable water solution of chemical salts providing an electrolytic solution to which a blood sample can be added to dilute the large number of red blood cells, white blood cells and other components and enable the desired parameters of these blood components to be measured, counted and determined.

BACKGROUND OF THE INVENTION

It is a common medical diagnostic procedure to analyze and test a blood sample of a patient in order to make certain classic determinations with respect to the blood sample. This procedure is an important tool for the physician. Six characteristically important parameters are referred to as red blood cell count (RBC), the hematrocrit (HCT), the hemoglobin (HGB), the mean corpuscular volume (MCV), the mean corpuscular hemoglobin (MCH) and the mean corpuscular hemoglobin concentration (MCHC). A seventh important determination is white blood cell count (WBC). An instrument which will accept a patient's blood sample and process the sample automatically and continuously to provide the parameters or determinations enumerated is described and claimed in U.S. Pat. Nos. 3,973,189 and 4,093,849. Said U.S. Pat. Nos. 3,973,189 and 4,093,849 provide acceptable definitions of said parameters and illuminate the problems to be solved in the handling of the blood sample as it is drawn through the fluid system of the patented apparatus.

Red blood cells are biconcave discs generally toroidal in shape. The inter membrane is elastic. Hemoglobin and other components are contained in the interior of the cell. The specific parameters of the red blood cell which it is clinically desirable to measure by the electronic instrumentation dictate the necessary characteristics of a suitable diluent.

For instance, it is desirable to know the volume within the red blood cell. Once this measurement is ascertained and the red blood cells have been counted, the packed cell volume or Hematocrit (HCT) can be computed. The diluent of the invention therefore must be an electrolyte which enables electronic measurements to be made. The diluent of the invention also should be capable of equilibrating and stabilizing the volume of red blood cells in the sample so that its cubic volume can be measured, namely, mean cell volume (MCV).

Counting of blood cells requires accurate and successful dilution of the blood sample drawn into its fluid system. Such analysis predicates certain diluent specifications essential to the successful and proper performance of the apparatus. For instance, the diluent must be capable of maintaining the chemical and physical integrity of blood corpuscles prior to and during the assay procedure. The blood cells are required to retain the same physical character in the diluted solution as exhibited in the undiluted sample. For this purpose, the blood diluent must be isotonic and osmotically balanced relative the solutions in the blood cells. The resistance of the red blood cells to lysing for purposes of hemoglobin determinations must not be altered in any way by the blood diluent.

A suitable blood diluent must be devoid of foreign particulate matter because the presence of foreign particles will result in the counting thereof as a blood cell or constituent. Thus, the blood diluent must be filtered free of particles exceeding 0.2 micron diameter at the time of manufacture. Concomitantly, the diluent must be bacteriostatic in nature so as to prevent the growth of microorganisms after packaging of the diluent. It has been recognized that a proper blood diluent for use with such electronic particle analysis apparatus and hemoglobinometer instruments must be unreactive and osmotically balanced if reproducible, accurate results are to be obtained.

Such electrolyte solutions used in blood cell counting and sizing are required to be of such concentration that the electrolyte ions exert an osmotic pressure equal to that of the intracellular fluid. If the cells are suspended in a solution of reduced osmotic pressure, that is, hypotonic, the cells will absorb water and expand until burst thereof releases the cell fluids into the solution. This condition is called "hemolysis". Where blood cells are suspended in an electrolyte solution of increased osmotic pressure, cellular fluid will be lost to the solution thereby shrinking the volume of the cell. This condition is called "crenation". Although preservatives for preventing bacterial or fungal growth are desirable, caution must be observed to avoid increasing the cell volume of blood cells in suspension by reason of the preservative used.

A blood diluent heretofore available for this purpose possessed certain undesirable features. For example, the use of sodium azide as a bacteriostatic agent in isotonic blood diluents presented several such undesirable features. Sodium azide is a relatively high toxic material so that aqueous solutions of the azide and vapors of hydrazoic acid were required to be taken into account as possibly contributing to adverse physiological effects on laboratory workers exposed to same. In the case of plumbing systems using copper and lead pipes and joints through which the azide solutions must be drained, it is necessary to exercise prudent and judicious flushing procedures to prevent excess accumulations of heavy metal azides over extended periods of time that could lead to potentially explosive circumstances.

Therefore, it was highly desirable to replace sodium azide with an equally effective bacteriostatic agent. In U.S. Pat. No. 3,962,125 issued June 8, 1976 to D. Armstrong, there is proposed the replacement of sodium azide with 2-phenoxyethanol as a bacteriostatic agent to eliminate the problems present with the use of diluents containing sodium azide. However, while the use of 2-phenoxyethanol substantially alleviated the problems attendant the use of sodium azide containing blood diluents, the newly proposed use of 2-phenoxyethanol has caused an undesired feature interfering with the counting of blood platelets due to the formation of bubbles caused by the detergent action of 2-phenoxyethanol. Thus it has now become highly desirable to provide a blood diluent with a bacteriostatic agent that does not have the drawbacks of a sodium azide containing diluent and which also does not present any significant problem due to bubble formation as caused by 2-phenoxyethanol.

SUMMARY OF THE INVENTION

A blood diluent of the desired characteristics and useful in the counting of blood cells is provided wherein phenylethanol is employed as the bacteriostatic and preserving agent and wherein lithium chloride is employed as a mean cell volume stabilizer.

DETAILED DESCRIPTION OF THE INVENTION

The blood diluent of this invention comprises an osmotically balanced and unreactive diluent wherein phenylethanol is employed as a bacteriostat in the formulation in an amount of from about 0.1 to about 1.0% by weight and preferably about 0.2 to about 0.5% and most preferably at about 0.2% by weight and wherein lithium chloride is employed as a mean cell stabilizer in the formulation in an amount of from about 0.03 to 0.1% by weight. The diluent is adjust to a pH of 7.2–7.5 by the suitable buffering agent, EDTA and phosphate salts.

The desirable characteristic of osmotic balance is procured through the use of both sodium and potassium chloride and the mono- and di-hydrogen phosphate salts of sodium and potassium.

An example of a multi-purpose blood diluent according to the invention is as follows:

| Component | Amount gram/liter | m ml/liter |
|---|---|---|
| Sodium chloride | 8.12 | 139 |
| Potassium chloride | 0.283 | 3.796 |
| Potassium dihydrogen phosphate | 0.258 | 1.896 |
| Disodium monohydrogen phosphate | 2.354 | 16.58 |
| Ethylenediamine tetraacetic acid disodium salt | 0.356 | 0.956 |
| Lithium chloride | 0.43 | 10 |
| Phenylethanol | 1.96 | 16 |
| Distilled water | dilute to 1 liter | |

This blood diluent solution which is an electrolyte capable of conducting current, stabilizes the red blood cells so that their cubic volume can be accurately measured and has no adverse effect on white blood cells and can function as an electrolyte for counting white blood cells by electronic methodology.

Preparation of the diluent does not require any special procedures or any special order of addition of ingredients to the water. Consequently, the invention does not concern any methodology in formulation of the diluent. The mixture of ingredients is done mechanically by moderate stirring over a one to two hour period. The solution then is filtered through a 0.2 micron filter and stored directly in plastic containers.

Although the preferred formulation has been specified above, the range of pH and osmolality may be broadened for useful purposes. Thus, the pH range may be maintained from between pH of 7.0 to 8.0, preferably 7.2 to 7.5. Likewise the useful range of osmolality can be between 300 to 380 milliosmoles, preferably 320 to 350 milliosmoles. This can be accomplished by varying the amount of active ingredients used for the purpose as specified herein.

I claim:

1. A multi-purpose blood diluent, which is both isotonic and osmotically balanced relative to the solutions in blood cells, comprising:
   (a) an osmotically balanced solution of the chlorides of sodium and potassium and the mono- and dihydrogen phosphate salts of sodium and potassium,
   (b) an ethylene diamine tetraacetic acid compound,
   (c) lithium chloride, and
   (d) phenylethanol, said diluent being an aqueous electrolytic solution maintained at a pH between 7.0 and 8.5 and at an osmolality between 300 and 380 milliosmoles.

2. The multi purpose diluent of claim 1 wherein the pH is maintained between pH 7.2 and 7.5 and the osmolality between 320 and 350 milliosmoles.

3. The multi-purpose diluent of claim 2 which comprises:

| | |
|---|---|
| 8.12 g/l | sodium chloride |
| 0.283 g/l | potassium chloride |
| 0.258 g/l | potassium dihydrogen phosphate |
| 0.354 g/l | disodium monohydrogen phosphate |
| 0.356 g/l | ethylenediamine tetraacetic acid disodium salt |
| 0.43 g/l | lithium chloride |
| 1.96 g/l | phenylethanol |
| dilute to 1 liter | distilled water |

* * * * *